(12) United States Patent
Bae et al.

(10) Patent No.: US 7,390,870 B2
(45) Date of Patent: Jun. 24, 2008

(54) IMMUNE-ENHANCING PEPTIDES

(75) Inventors: Hyunjoo Bae, Daegu (KR); Yoe-Sik Bae, Kyungsanbuk-do (KR); Youn-Dong Kim, Kyungsangbuk-do (KR); Tae-Hoon Lee, Kyungsangbuk-do (KR); Pann-Ghill Suh, Kyungsangbuk-do (KR); Sung-Ho Ryu, Kyungsangbuk-do (KR)

(73) Assignees: Posco (KR); Pohang University of Science & Technology (KR)

( * ) Notice: Subject to any disclaimer, the term of this patent is extended or adjusted under 35 U.S.C. 154(b) by 428 days.

(21) Appl. No.: 10/186,035

(22) Filed: Jun. 28, 2002

(65) Prior Publication Data

US 2003/0055001 A1    Mar. 20, 2003

Related U.S. Application Data

(60) Provisional application No. 60/302,744, filed on Jul. 3, 2001.

(51) Int. Cl.
*A61K 38/00* (2006.01)
*A61K 39/00* (2006.01)
*C07K 16/00* (2006.01)

(52) U.S. Cl. ..................................... 530/300; 424/184.1
(58) Field of Classification Search ....................... None
See application file for complete search history.

(56) References Cited

U.S. PATENT DOCUMENTS 6,184,208 B1 *   2/2001   Deigin et al. ................. 514/17

OTHER PUBLICATIONS

Bae et al Blood. 2001;97:2854-2862.*
Webster's Seventh New Collegiate Dictionary. 1965, p. 846. Published by G&C Merriam Company, Springfield, Massachusetts, USA.*

* cited by examiner

*Primary Examiner*—Maher M. Haddad
*Assistant Examiner*—Chun Crowder
(74) *Attorney, Agent, or Firm*—Baker & Hostetler, LLP

(57) ABSTRACT

Disclosed are peptides having SEQ ID NOs: 1 to 32 that can stimulate superoxide generation in human monocytes. Superoxide is the most important armory on the primary defense line of monocytes against invading pathogens, and the identification of new stimuli and the characterization of the regulatory mechanism of superoxide generation are of paramount importance.

8 Claims, 10 Drawing Sheets

IMMUNE-ENHANCING PEPTIDES

CROSS REFERENCE TO RELATED APPLICATIONS

This application claims the benefit under 35 U.S.C. §119 (e) of the U.S. Provisional Application Ser. No. 60/302,744, entitled "IMMUNE-ENHANCING PEPTIDE", filed Jul. 3, 2001.

BACKGROUND OF THE INVENTION (a) Field of the Invention

The present invention relates to an immune-enhancing peptide, and more specifically to an immune-enhancing peptide that can induce superoxide generation in human monocytes.

(b) Description of the Related Art

Reactive oxygen species (ROS) such as superoxide, hydrogen peroxide, and hydroxyl radicals are generated by phagocytic cells upon activation by invading microorganisms or inflammatory debris (1, 2). The production of these ROS enables the phagocytes such as monocytes to play a critical role in human immune responses. The activation of the ROS generation system, which is one of the earliest steps in the host defense against invading microorganisms, is tightly regulated in the immune systems (1-3). To perform their proper roles, monocytes in the resting state have to be activated, and this is a very critical aspect of the host defense mechanism.

Monocyte activation can be induced by various extracellular stimuli such as bacterial endotoxins (lipopolysaccharides), immunoglobulins, and several chemoattractants (4-7). Among these extracellular stimuli, chemoattractants including several chemokines that regulate the activities of monocytes have been receiving attention for a long time. Many chemoattractants stimulate leukocytes via the activation of pertussis toxin (PTX)-sensitive G-protein-coupled receptors (1). Upon binding to its corresponding cell surface receptor, a chemoattractant induces intracellular $Ca^{2+}$ mobilization, cytoskeletal rearrangements, exocytosis, histamine release, receptor induction, adhesion, the production of bioactive lipids, and the activation of the respiratory burst system via NADPH oxidase activation (1, 8, 9). With this important role of chemoattractants for monocyte functions in mind, the identification of new chemoattractants and the characterization of their mechanisms of action are very much needed.

Recently, several studies have reported the use of combinatorial peptide libraries to identify sequences involved in various biological responses. Houghten et al. developed a method for a positional scanning synthetic peptide combinatorial library (PS-SPCL) that is an easy and powerful tool for identifying peptide sequences in certain biological reactions (10). This method has been adopted for various purposes including the identification of human immunodeficiency virus protease inhibitors, interleukin-8-specific antagonists, inhibitors for nuclear factors of activated T cells, and ligands for opioid receptors (11-14). Also, the present inventors have already identified one bioactive hexapeptide that stimulates phosphoinositide hydrolysis, by screening hexapeptide combinatorial libraries (15). However, the research thus far has been very limited, and therefore there are continuing demands for identifying novel agents.

SUMMARY OF THE INVENTION

It is an object of the present invention to provide an immune-enhancing peptide that can induce superoxide generation in human monocytes.

In order to accomplish these and other objects, the present invention provides a peptide comprising SEQ ID NO: 1 to SEQ ID NO: 32 which can stimulate human monocytes leading to superoxide generation.

It is another object to provide a pharmaceutical composition comprising a peptide having an amino sequence selected from SEQ ID NO: 1 to SEQ ID NO: 32 which can stimulate human monocytes leading to superoxide generation; or a substance derived from a peptide of which its amino acid sequence is selected from the group consisting of SEQ ID NO: 1 to SEQ ID NO: 32.

It is still another object to provide a method of treating condition accompanied or caused by modification of the number or activation state of leukocytes comprising administering to a host in need of such treatment an effective amount of the peptides whose complete amino acid sequences comprise SEQ ID NO: 1 to SEQ ID NO: 32.

It is further object to provide a method of increasing the number or raising the activation state of leukocytes in a host comprising administering to a host in need of a greater number or higher activation state of leukocytes a therapeutically effective amount of the peptides whose complete amino acid sequences comprise SEQ ID NO: 1 to SEQ ID NO: 32.

It is still further object to provide a method of inducing superoxide generation by human monocytes or neutrophils, in a patient in need of such treatment, the method comprising administering to said patient an amount of the peptides whose complete amino acid sequences comprise SEQ ID NO: 1 to SEQ ID NO: 32 in an amount effective to therapeutically or prophylactically achieve such induction or desensitization.

It is still further object to provide a method of inducing intracellular calcium increase in leukocytes, in a patient in need of such treatment, the method comprising administering to said patient an amount of the peptides whose complete amino acid sequences comprise SEQ ID NO: 1 to SEQ ID NO: 32 in an amount effective to therapeutically or prophylactically achieve such induction or desensitization.

It is still further object to provide a method of inducing chemotactic migration by human peripheral blood mononuclear cells, in a patient in need of such treatment, the method comprising administering to said patient an amount of the peptides whose complete amino acid sequences comprise SEQ ID NO: 1 to SEQ ID NO: 32 in an amount effective to therapeutically or prophylactically achieve such induction or desensitization.

It is still further object to provide a method of desensitizing fMLP-induced intracellular calcium increase in human monocytes, in a patient in need of such treatment, the method comprising administering to said patient an amount of the peptides whose complete amino acid sequences comprise SEQ ID NO: 1 to SEQ ID NO: 32 in an amount effective to therapeutically or prophylactically achieve such induction or desensitization.

It is still further object to provide an isolated nucleotide encoding the peptides whose complete amino acid sequences comprise SEQ ID NO: 1 to SEQ ID NO: 32.

It is still further object to provide a vector comprising an isolated nucleotide encoding the peptides whose complete amino acid sequences comprise SEQ ID NO: 1 to SEQ ID NO: 32.

Other features and advantages of the present invention will be apparent from the following description taken in conjunc-

BRIEF DESCRIPTION OF THE DRAWINGS

The accompanying drawings, which are incorporated in and constitute a part of the specification, illustrate embodiments of the invention, and together with the description, serve to explain the principles of the invention.

DETAILED DESCRIPTION OF THE PREFERRED EMBODIMENTS

Figure 1:
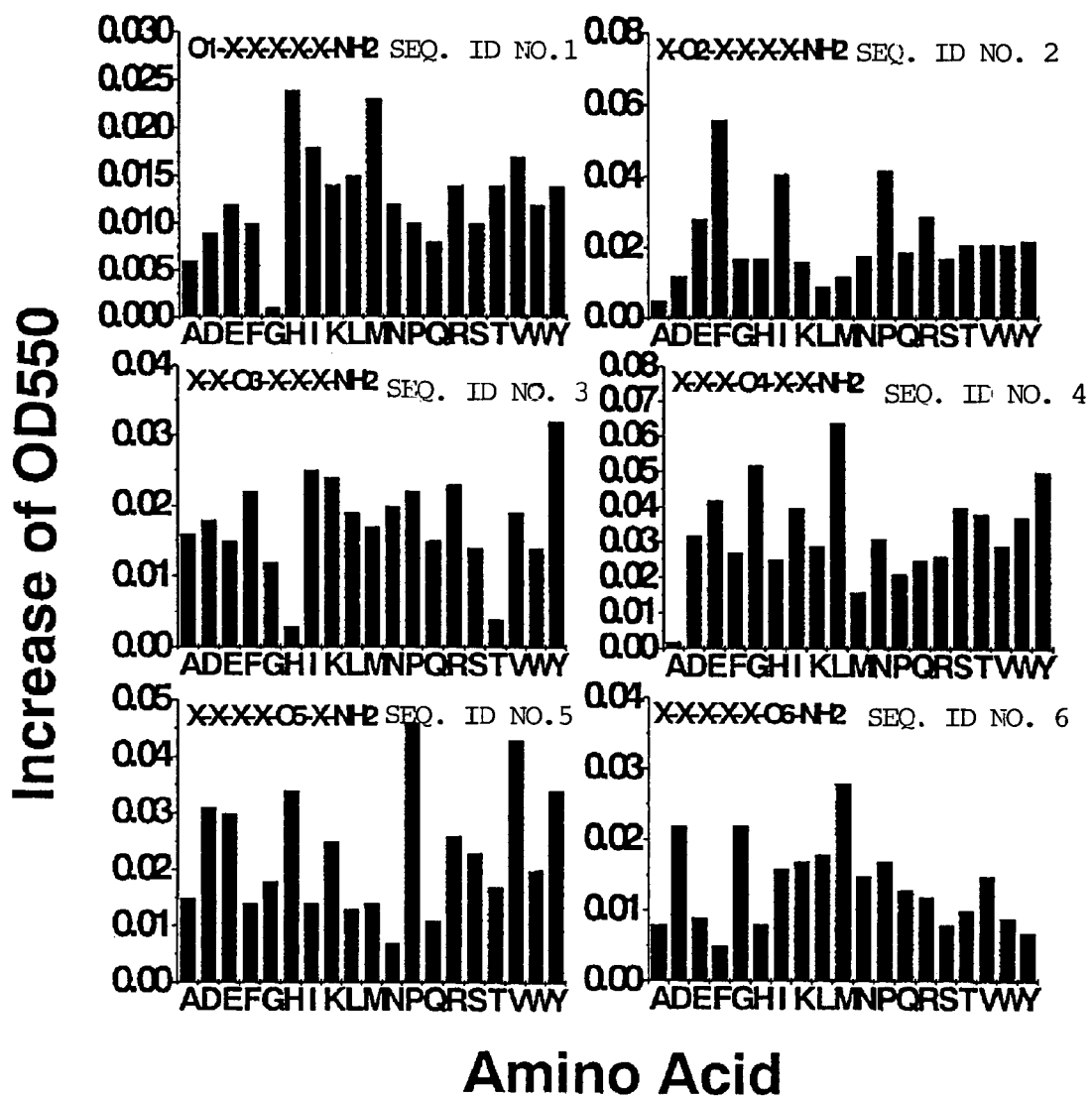
FIG. 1 shows the results of the initial screening of the PS-SPCLs to identify peptides that stimulate superoxide generation in human monocytes.

An organism has to defend itself against invading pathogens in order to survive. Therefore, hosts have developed efficient defense mechanisms. Phagocytic cells including monocytes, macrophages, and neutrophils have important roles in the earliest defenses against pathogens and other harmful agents (1-3). Since ROS including superoxides are part of the armory of the host defense system against invading microorganisms, the identification of novel agents that can modulate phagocyte function and help to elucidate its actions is of paramount importance.

The present invention provides novel peptides that can stimulate superoxide generation in human monocytes. The novel peptides of the present invention that can stimulate superoxide generation in human monocytes were identified by using the positional scanning synthetic peptide combinatorial library (PS-SPCL) method, and by modification of the identified peptides. Using the PS-SPCL method, the screening of hexapeptide combinatorial libraries that contain more than 47 million different peptide sequences was adopted, and the peptides comprising SEQ ID NO: 1 to SEQ ID NO: 32 that can stimulate human monocytes leading to superoxide generation were identified. The peptides of the present invention activate leukocytes, and they exist in isolated and substantially pure form.

The identified peptide comprises amino sequences selected from the group consisting of:
His-Phe-Tyr-Leu-Pro-Met (SEQ ID NO: 1), Met-Phe-Tyr-Leu-Pro-Met (SEQ ID NO: 2) His-Phe-Tyr-Leu-Pro-D-type-Met (SEQ ID NO: 3), Met-Phe-Tyr-Leu-Pro-Gly (SEQ ID NO: 4), Met-Phe-Tyr-Leu-Pro-Asp (SEQ ID NO: 5), His-Phe-Tyr-Leu-Pro-Gly (SEQ ID NO: 6), His-Phe-Tyr-Leu-Pro-Asp (SEQ ID NO: 7), Met-Phe-Tyr-Leu-Val-Gly (SEQ ID NO: 8), Met-Phe-Tyr-Leu-Val-Asp (SEQ ID NO: 9), Met-Phe-Tyr-Leu-Val-Met (SEQ ID NO: 10), His-Phe-Tyr-Leu-Val-Gly (SEQ ID NO: 11), His-Phe-Tyr-Leu-Val-Asp (SEQ ID NO: 12) His-Phe-Tyr-Leu-Val-Met (SEQ ID NO: 13), Met-Phe-Tyr-Leu-Pro-D-type-Met (SEQ ID NO: 14), His-Phe-Tyr-Leu-Val-D-type-Met (SEQ ID NO: 15), Met-Phe-Tyr-Leu-Val-D-type-Met (SEQ ID NO: 16), His-Phe-Tyr-Leu-Pro-D-type-Gly (SEQ ID NO: 17), His-Phe-Tyr-Leu-Pro-D-type-Asp (SEQ ID NO: 18), Met-Phe-Tyr-Leu-Pro-D-type-Gly (SEQ ID NO: 19), Met-Phe-Tyr-Leu-Pro-D-type-Asp (SEQ ID NO: 20), His-Phe-Tyr-Leu-Val-D-type-Gly (SEQ ID NO: 21), His-Phe-Tyr-Leu-Val-D-type-Asp (SEQ ID NO: 22), Met-Phe-Tyr-Leu-Val-D-type-Gly (SEQ ID NO: 23), Met-Phe-Tyr-Leu-Val-D-type-Asp (SEQ ID NO: 24), Met-Phe-Tyr-Leu-Pro-Xaa (SEQ ID NO: 25), His-Phe-Tyr-Leu-Pro-Xaa (SEQ ID NO: 26), Met-Phe-Tyr-Leu-Val-Xaa (SEQ ID NO: 27), His-Phe-Tyr-Leu-Val-Xaa (SEQ ID NO: 28), Met-Phe-Tyr-Leu-Pro-Xaa (SEQ ID NO: 29), His-Phe-Tyr-Leu-Pro-Xaa (SEQ ID NO: 30), Met-Phe-Tyr-Leu-Val-Xaa (SEQ ID NO: 31), and His-Phe-Tyr-Leu-Val-Xaa (SEQ ID NO: 32).

The peptides of SEQ ID NO: 1 to SEQ ID NO: 32 include sixth amino acid residue optionally substituted with a —NH$_2$ group on a carboxyl group.

One preferable embodiment of the present invention is a substance derived from the peptide of SEQ ID NO: 1 to SEQ ID NO: 32. The substance is a peptide amounting to 6 amino acids, said peptide comprising the following sequence:

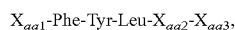

$X_{aa1}$-Phe-Tyr-Leu-$X_{aa2}$-$X_{aa3}$, wherein
$X_{aa1}$ is His or Met,
$X_{aa2}$ is Pro or Val, and
$X_{aa3}$ is selected from the group consisting of Asp, Gly, Met, D-type Asp, D-type Gly, and D-type Met,
and which has at least one of the following properties:
(a) it induces superoxide generation by human monocytes or neutrophils;
(b) it induces an intracellular calcium increase by human peripheral blood monocytes or neutrophils;
(c) it induces an intracellular calcium increase by U937, HL60, differentiated HL60, or Jurkat cells;
(d) it induces chemotactic migration of human monocytes or neutrophils in vitro; and
(e) it desensitizes an fMLP-induced intracellular calcium increase.

According to another preferable embodiment of the present invention, His-Phe-Tyr-Leu-Pro-Met-CONH$_2$ (SEQ ID NO.: 1, hereinafter referred to as "HFYLPM"), Met-Phe-Tyr-Leu-Pro-Met-CONH$_2$ (SEQ ID NO.: 2, hereinafter referred to as "MFYLPM"), and His-Phe-Tyr-Leu-Pro-D-Met-CONH$_2$ (SEQ ID NO.: 3, hereinafter referred to as "HFYLPm") which has been modified from HFYLPM are provided. All these peptides also cause an intracellular calcium ($[Ca^{2+}]_i$) increase and induce chemotactic migration in human monocytes.

The novel hexapeptides HFYLPM (SEQ ID NO: 1) and MFYLPM (SEQ ID NO: 2) can induce superoxide generation in human monocytes at a high level. An analogue of HFYLPM, HFYLPm (SEQ ID NO: 2), was also developed as a potent stimulator for human leukocytes.

The peptides of the present invention have the specificities on cells of different origins by looking at $[Ca^{2+}]_i$ increases. All three peptides act specifically on leukocytes and not on non-immune cells. Among leukocytes, HL60 and Jurkat T cells are stimulated specifically by MFYLPM or HFYLPM, respectively. As a physiological characteristic of the peptides, it is observed that all three peptides induce chemotactic migration of monocytes. By studying receptor specificity, the fact that the three peptides might act on some shared and some distinct receptor(s) on leukocytes was concluded. Studying intracellular signaling set in motion by the peptides revealed that HFYLPM, but not MFYLPM or HFYLPm, induced chemotaxis via phospatidylinositol-3-kinase and protein kinase C. Since HFYLPM, MFYLPM, and HFYLPm not only exhibit different specificities depending on cell type and status of differentiation, but also stimulate cells via distinct receptors and signaling pathways, the three novel peptides might be useful tools to study leukocyte activation.

The present invention also provides a pharmaceutical composition comprising a peptide of which the amino acid sequence is selected from the group consisting of SEQ ID NO: 1 to SEQ ID NO: 32; or a substance derived from a peptide of which the amino acid sequence is selected from the group consisting of SEQ ID NO: 1 to SEQ ID NO: 32.

The composition comprising the peptide or the substance as an active ingredient can include more than one kind of pharmaceutical diluent, selected from the group consisting of saline, buffered saline, dextrose, water, glycerol, and ethanol, but the diluent is not limited thereto.

The composition may be applied differently according to the purpose of dosing and diseases. It should be understood that the amount of the active ingredient actually administered ought to be determined in light of various relevant factors including the condition to be treated, the severity of the patient's symptoms, co-administration with other drugs (e. g., chemotherapeutic agents), age, sex, body weight of the individual patient, food, dosing time, the chosen route of administration, and the ratio of the composition. The composition may be administrated in a single or in 1-3 divided doses per day, even though the dose and route of administration are adjusted to the type and severity of disease.

The composition comprising the peptide or the substance of the present invention can be administered via oral or parenteral routes. Parenteral dosing means the administration of a drug through a route other than oral, which includes rectal, intravenous, intraperitoneal and intramuscular, intra-arterial, transdermal, nasal, inhalation, ocular, and subcutaneous introduction.

Pharmaceutical formulations containing the peptide or the substance may be prepared in any form, such as oral dosage form, injectable solution, or topical preparation. The formulation can be preferably prepared for oral and injectable administration (true solution, suspension, or emulsion) and most preferably in oral form such as tablet, capsule, soft capsule, aqueous medicine, pill, granule, and the like.

In preparing the formulation, the peptides are filled in the soft capsule without any excipient, or formed as an appropriate formulation after mixing or diluting with a carrier. Examples of suitable carriers are starches, water, saline, Ringer's solution, dextrose, etc.

According to another preferable embodiment of the present invention, a method of treating conditions accompanied or caused by modification of the number or activation state of leukocytes is provided. The method comprises administering to a host in need of such treatment an effective amount of the peptides whose complete amino acid sequences comprise SEQ ID NO: 1 to SEQ ID NO: 32. The condition may be bacterial, mycoplasma, yeast, fungal, or viral infection or inflammation.

According to another preferable embodiment of the present invention, a method of increasing the number or raising the activation state of leukocytes in a host is provided. The method comprises administering a therapeutically effective amount of the peptides whose complete amino acid sequences comprise SEQ ID NO: 1 to SEQ ID NO: 32 to a host in need of a greater number or higher activation state of leukocytes. Said host may be a patient afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

According to another preferable embodiment of the present invention, a method of inducing superoxide generation by human monocytes or neutrophils in a patient in need of such treatment is provided. The method comprises administering to said patient an amount of the peptides whose complete amino acid sequences comprise SEQ ID NO: 1 to SEQ ID NO: 32 in an amount effective to therapeutically or prophylactically achieve such induction or desensitization. The treated subject may be a patient afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

According to another preferable embodiment of the present invention, a method of inducing intracellular calcium increase in leukocytes in a patient in need of such treatment is provided. The method comprises administering to said patient an amount of the peptides whose complete amino acid sequences comprise SEQ ID NO: 1 to SEQ ID NO: 32 in an amount effective to therapeutically or prophylactically achieve such induction or desensitization. The treated subject may be a patient afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

According to another preferable embodiment of the present invention, a method of inducing chemotactic migration by human peripheral blood mononuclear cells in a patient in need of such treatment is provided. The method comprises administering to said patient an amount of the peptides whose complete amino acid sequences comprise SEQ ID NO: 1 to SEQ ID NO: 32 in an amount effective to therapeutically or prophylactically achieve such induction or desensitization. The treated subject may be a patient afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

According to another preferable embodiment of the present invention, a method of desensitizing an fMLP-induced intracellular calcium increase in human monocytes, in a patient in need of such treatment is provided. The method comprises administering to said patient an amount of the peptides whose complete amino acid sequences comprise SEQ ID NO: 1 to SEQ ID NO: 32 in an amount effective to therapeutically or prophylactically achieve such induction or desensitization. The treated subject may be a patient afflicted with a disorder caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, or alopecia.

The present invention provides a isolated nucleotide encoding the peptides whose complete amino acid sequences comprise SEQ ID NO: 1 to SEQ ID NO: 32.

The present invention provides a vector comprising an isolated nucleotide encoding the peptides whose complete amino acid sequences comprise SEQ ID NO: 1 to SEQ ID NO: 32.

The present invention provides a polypeptide comprising an amino sequence selected from SEQ ID NO: 1 to SEQ ID NO: 32.

The present invention is further explained in more detail with reference to the following examples. These examples, however, should not in any sense be interpreted as limiting the scope of the present invention.

The results in the below examples are expressed as means ±S.E. of data obtained from the indicated number of experiments performed if they are not defined specifically. Statistical significance was determined using the Student t test.

MATERIALS USED IN THE EXAMPLES

Fmoc amino acids were obtained from Millipore (Bedford, Mass.). Rapidamide resin was purchased from Dupont (Boston, Mass.). Peripheral blood mononuclear cells (PBMCs) separation medium (Histopaque-1077), cytochrome c, and fMLF were purchased from Sigma (St. Louis, Mo.). Fura-2 pentaacetoxymethylester (fura-2/AM) was purchased from Molecular Probes (Eugene, Oreg.). The RPMI 1640 was obtained from Life Technologies (Grand Island, N.Y.). Dialyzed fetal bovine serum and supplemented bovine serum were purchased from Hyclone Laboratories Inc. (Logen, Utah). PTX, GF109203X, and PD98059 were purchased from Calbiochem (San Diego, Calif.). LY294002 was from BIOMOL research laboratories, Inc (Plymouth Meeting, Pa.).

Example 1

Isolation of Leukocytes

Peripheral blood leukocyte concentrates were donated by the Ulsan Red Cross Blood Center (Ulsan, Korea). Peripheral blood mononuclear cells (PBMCs) were separated on a Histopaque-1077 gradient. After washing twice with Hanks' balanced salt solution (HBSS) without $Ca^{2+}$ and $Mg^{2+}$, the PBMCs were suspended in 10% FBS containing RPMI and incubated for 60 minutes at 37° C. to let the monocytes attach to the culture dish. The cells were washed 5 times with warmed RPMI medium to wash out lymphocytes, and then the attached monocytes were collected as described previously (16). Human neutrophils were isolated according to the standard procedures of dextran sedimentation, hypotonic lysis of erythrocytes, and a lymphocyte separation medium gradient as described previously (17). The isolated human leukocytes were then used promptly.

Example 2

Cell Culture and HL60 Cell Differentiation

U937 (human histiocytic lymphoma cells), HL60 (human promyelocytic leukemia cells), Jurkat (human T cell leukemia cells), NIH3T3 (NIH Swiss mouse embryo fibroblasts), 3Y1 (Rat embryonic fibroblasts), 3T3L1 (preadipocytes), and PC12 (rat adrenal pheochromocytoma cells) were obtained from the American Type Culture Collection (Rockville, Md.) and maintained as re, commended. The cells were maintained at about $1\times10^6$ cells/ml under standard incubator conditions (humidified atmosphere, 95% air, 5% $CO_2$, 37° C.). HL60 cells were induced to differentiate into the granulocyte phenotype by adding dimethylsulfoxide (DMSO) (final concentration 1.25%, v/v) for 4 days to the culture medium as has been described before (18).

Example 3

Preparation of Peptide Libraries and Synthesis and Analysis of Peptides

The hexapeptide libraries were prepared in the Peptide Library Support Facility of Pohang University of Science and Technology as described previously (15, 19). Finally, 114 peptide pools (Cys was excluded in the construction of the libraries) were individually dissolved in water at a final concentration of 27 nM per peptide sequence in each pool. The peptides were synthesized by the solid-phase method described before (15, 19). Briefly, peptides were synthesized on a rapidamide support resin and assembled following the standard Fmoc/t-butyl strategy on an acid-labile linker. The composition of the peptides was confirmed by amino acid analysis as described previously (15).

Example 4

Initial Screening of the PS-SPCLs and Measurement of Superoxide Generation

For initial screening of the PS-SPCLs, the superoxide anion generation of each peptide pool was evaluated by measuring reduction of cytochrome c using a microtiter 96 well plate ELISA reader (Bio-Tekinstruments, EL312e, Winooski, Vt.) as described (20). The cytochrome c was purchased from Sigma (St. Louis, Mo.). The human monocytes ($9\times10^5$ cells/100 □ of RPMI 1640 medium per well of a 96-well plate) were preincubated with 50 μM cytochrome c at 37° C. for 1 minute and then incubated with the indicated concentrations of peptide pools (final 0.5 nM per peptide sequence for the initial screening). The superoxide generation was measured as change in light absorption at 550 nm over 5 minutes at 1 minute intervals. From at least four independent experiments, peptides with active amino acids at each position were chosen. Superoxide generation by the identified peptides was measured by the same method. Spurious reduction of cytochrome c was ruled out by checking that the peptides-induced ones were superoxide dismutase-inhibitable in all experiments.

Each panel showed the results obtained with the peptide pools with known amino acids at each of the six positions of the hexapeptide. The six positions were individually defined (O1, O2 etc. of FIG. 1) by one of the 19 L-amino acids. The remaining five positions consisted of mixtures (X) of the 19 L-amino acids (except for cysteine). Human monocytes ($9\times10^5$ cells/100 □) were used for each assay.

A total of 114 peptide pools (around 47 million peptides) were screened from hexapeptide PS-SPCLs to identify peptides that stimulate superoxide generation in human monocytes. FIG. 1 shows the results of one of four independent experiments of the initial screening.

The present inventor observed that each amino acid that was fixed at each position induced different levels of superoxide generation. The most active peptides for each position were as follows: His (H) or Met (M) in the 1st position, Phe (F) in 2nd, Tyr (Y) in 3rd, Leu (L) in 4th, Pro (P) or Val (V) in 5th, and Met (M), Asp (D), or Gly (G) in 6th.

Example 5

Figure 2:
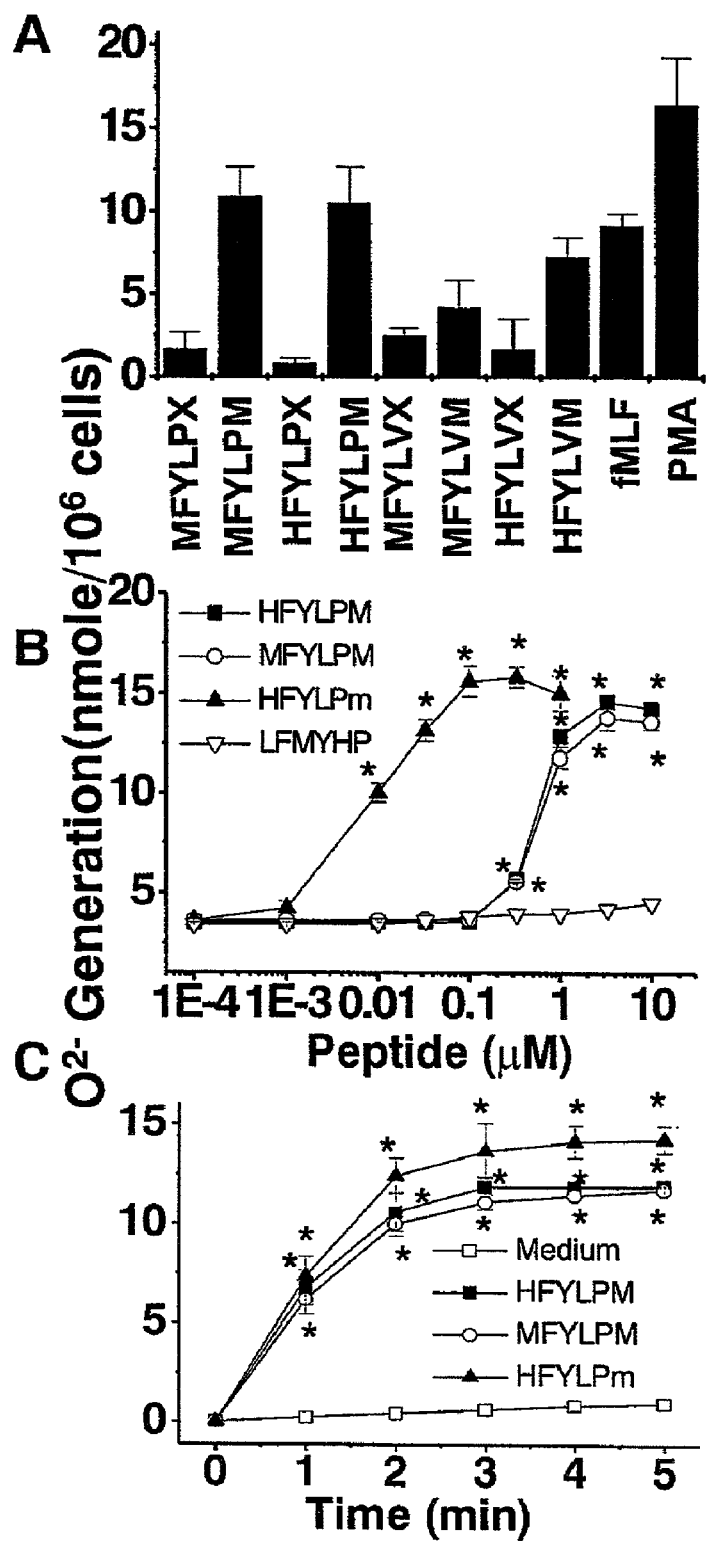
FIG. 2 shows the effect of the synthesized peptides of Example 5 of the present invention based on the screening results of the PS-SPCLs on superoxide generation in human monocytes (A); the concentration dependency of the superoxide generation induced by the synthesized peptides of Example 5 (B); and the time course of the peptides-induced superoxide generation in human monocytes (C)

Identification of Peptides That Stimulate Superoxide Generation in Human Monocytes Based on the results of the initial screening of the peptide libraries of Example 4, a peptide pool containing twelve ($2\times1\times1\times1\times2\times3=12$) individual hexapeptides were generated by reiterative synthesis. The peptide mixture was purified into 8 fractions that contained MFYLPX (SEQ ID NOs: 4 and 5), MFYLPM(SEQ ID NO: 2), HFYLPX (SEQ ID NOs: 6 and 7), HFYLPM (SEQ ID NO: 1), MFYLVX (SEQ ID NOs: 8 and 9), MFYLVM(SEQ ID NO: 10), HFYLVX (SEQ ID NOs: 11 and 12), and HFYLVM (SEQ ID NO: 13), where X is D or G, by reverse-phase HPLC with a C18 column (Vydac, 218TP1022, 22×250 mm). Then the effectiveness of the twelve peptides for the superoxide generation in human monocytes was tested by the same method as used in the initial screening of Example 1. FIG. 2 shows the results. The results of FIG. 2 are presented as means±S.E. of three independent experiments. *P<0.01 versus vehicle treatment.

The superoxide generated was measured using a cytochrome c reduction assay as described above. As shown in FIG. 2A, human monocytes were stimulated with 1 M concentrations of several peptides, 1 μM N-formyl-methionyl-leucyl-phenylalanine (fMLF), or 100 nM PMA. Among the identified peptides, HFYLPM and MFYLPM were the most active peptides in terms of superoxide generation by human monocytes. FIG. 2B illustrates the effect of concentration of the identified peptides on superoxide generation. As illustrated in FIG. 2B, the superoxide generation induced by peptides in monocytes shows the concentration dependency. The stimulation of monocytes with various concentrations of the two peptides induced superoxide generation in a concentration dependent manner with maximal activity at 3.3 μM. In FIG. 2B, HFYLPm is a modified peptide from HFYLPM by substitution of the 6th Met from an L-type to D-type. As a result, the HFYLPm enhanced superoxide generation showing the maximal activity with around 100 nM. FIG. 2C shows the time course of the peptides-induced superoxide generation in human monocytes. 3.3 μM of the HFYLPM and 330 nM of HFYLPm were used. As in FIG. 2C, the peptide-stimulated superoxide generation was rapid, showing the maximal effect within 3 minutes of the stimulation.

Example 6

Measurement of $[Ca^{2+}]_i$ and Effect of Novel Peptides on $[Ca^{2+}]_i$ a Rise in Human Monocytes The level of $[Ca^{2+}]_i$ was determined by Grynkiewicz's method using fura-2/AM (21). Briefly, prepared cells were incubated with 3 μM fura-2/AM at 37° C. for 50 minutes in a fresh serum-free RPMI 1640 medium under continuous stirring. $2\times10^6$ cells were aliquoted for each assay in $Ca^{2+}$-free Locke's solution (154 mM NaCl, 5.6 mM KCl 1.2 mM $MgCl_2$, 5 mM HEPES, pH 7.3, 10 mM glucose, and 0.2 mM EGTA). The fluorescence changes at the dual excitation wavelengths of 340 nm and 380 nm and the emission wavelength of 500 nm were measured, and the calibrated fluorescence ratio was translated into $[Ca^{2+}]_i$.

Figure 3:
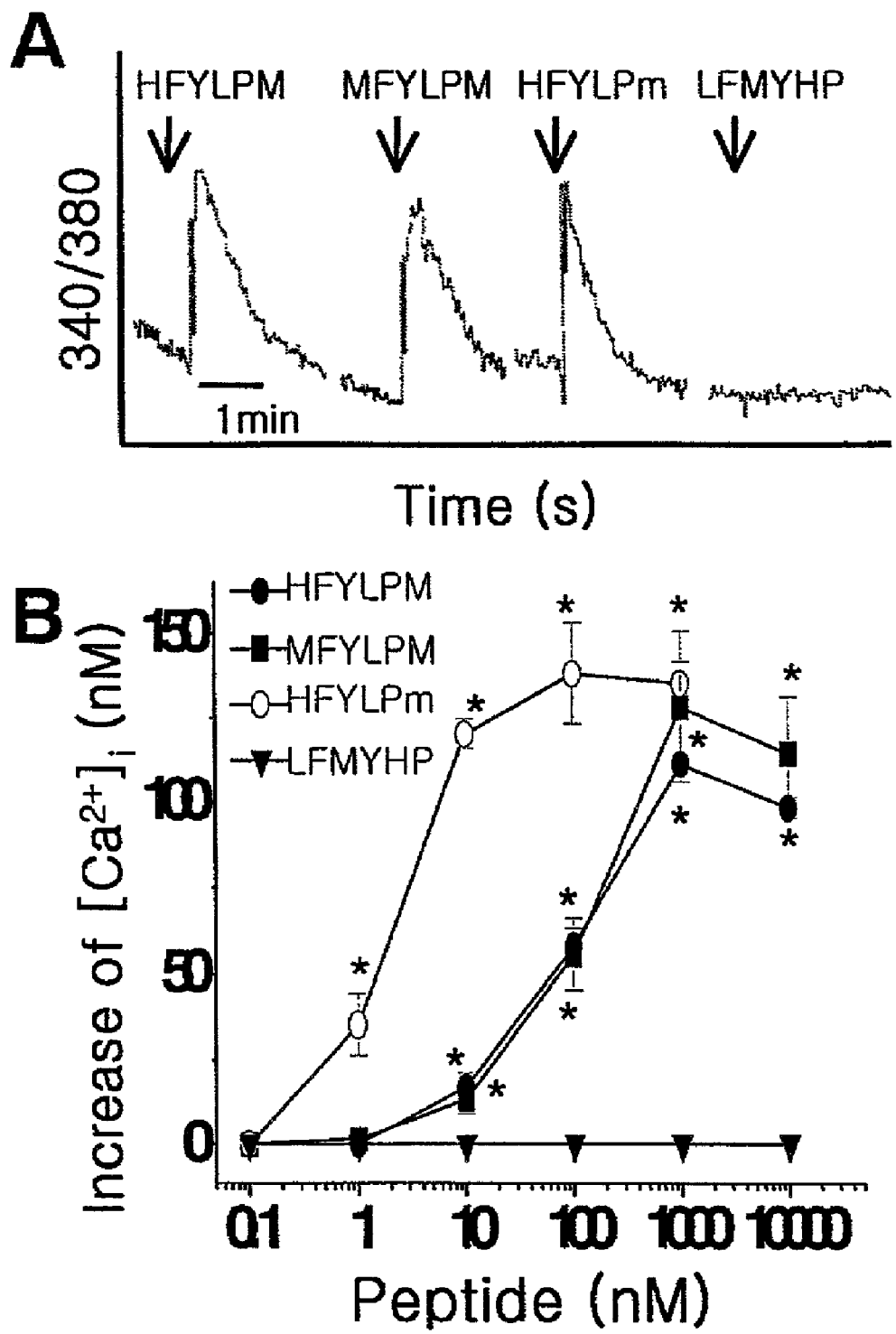
FIG. 3 shows the effect of peptides on $[Ca^{2+}]_i$ rise in human monocytes; a representative results of 6 independent experiments (A); and data of means±S.E. of 4 independent experiments (B).

Many extracellular agonists that stimulate superoxide generation in human phagocytic cells involve intracellular calcium rise (23). In this example, the effect of the peptides on the $[Ca^{2+}]_i$ of monocytes were tested. The results are shown FIG. 3. The data of FIG. 3 are presented as means ±S.E. of four independent experiments. *P<0.01 versus vehicle treatment.

Fura-2-loaded monocytes were stimulated with an effective concentration of HFYLPM (1 µM), MFYLPM (1 µM), HFYLPm (100 nM), and LFMYHP (10 µM). The change in 340 nm/380 nm was monitored. The cells were stimulated with various concentrations of each peptide. The peak level of the increase in $[Ca^{2+}]_i$ was monitored. As shown in FIG. 3A, HFYLPM (SEQ ID NO: 1), MFYLPM (SEQ ID NO: 2), and HFYLPm (SEQ ID NO: 3) caused intracellular Ca mobilization in monocytes. A scrambled sequence of the HFYLPM, LFMYHP did not affect $[Ca^{2+}]_i$ in the cells (FIG. 3A). The results of A of FIG. 3 are representative of 6 independent experiments. Concentration-dependency of the peptides-induced intracellular $Ca^{2+}$ mobilization was checked. HFYLPM and MFYLPM showed maximal $[Ca^{2+}]_i$ increases at 1 µM concentrations (FIG. 3B). HFYLPm could stimulate the monocytes at a lower concentration showing a maximal effect at 100 nM (FIG. 3B). A scrambled sequence of the HFYLPM and LFMYHP had no effect on the $[Ca^{2+}]_i$ increase up to 10 µM stimulation (FIG. 3B).

Example 7

Cell Type Specificity of the Novel Peptides

Figure 4:
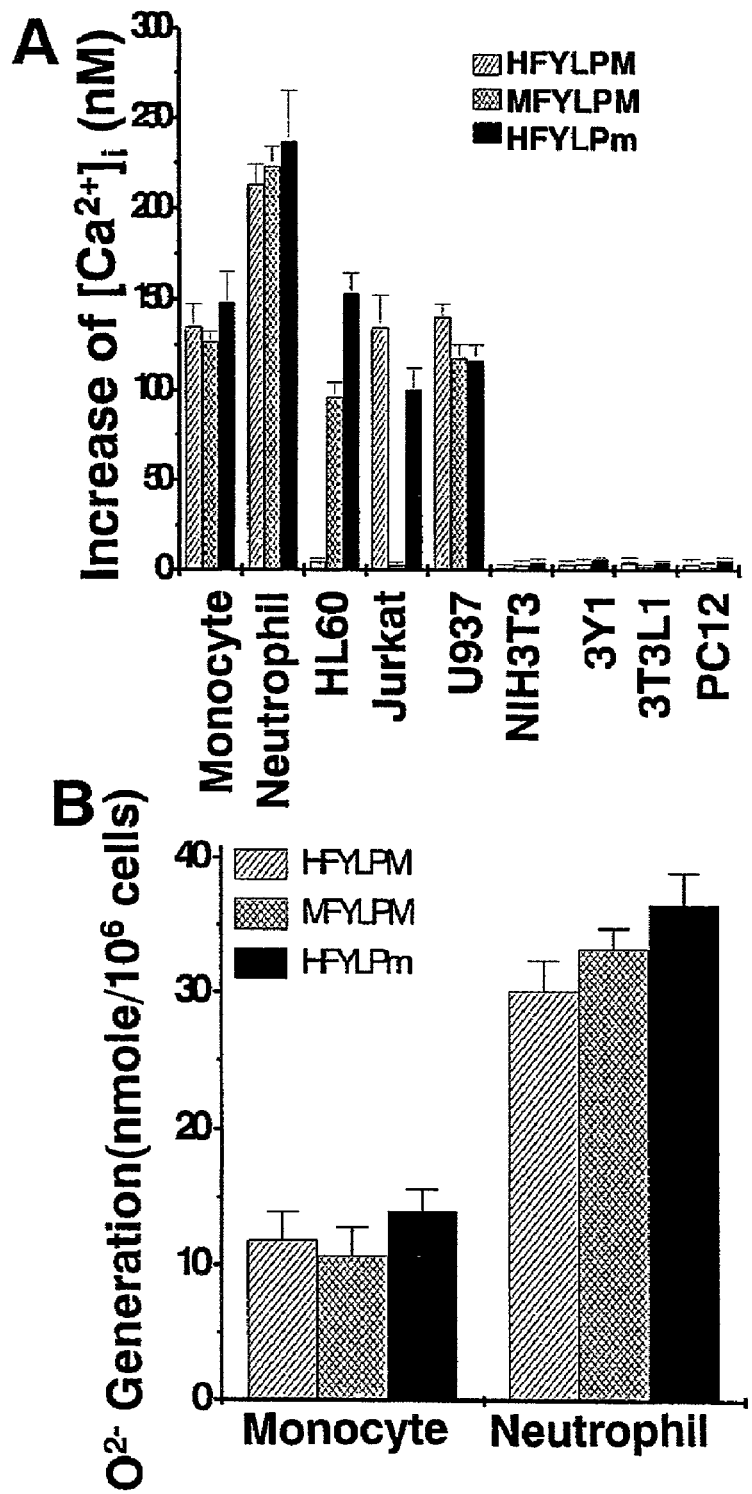
FIG. 4 shows the $[Ca^{2+}]_i$ increase recorded in various cells, human primary monocytes, neutrophils, cultured HL60, Jurkat, U937, NIH3T3, 3Y1, 3T3L1, and PC12 cells (A); and superoxide generation measured using a cytochrome c reduction assay (B)

From the fact that HFYLPM, MFYLPM, and HFYLPm stimulate human monocytes, effects of the peptides on other leukocytes such as neutrophils were evaluated. Prepared human primary monocytes, neutrophils, cultured HL60, Jurkat, U937, NIH3T3, 3Y1, 3T3L1, and PC12 cells were loaded with fura-2 and stimulated with effective concentrations of the three peptides (1 µM for monocyte and neutrophil; 10 µM for HL60 and Jurkat; 20 µM for U937, NIH3T3, 3Y1, 3T3L1, and PC12). The peak level of the $[Ca^{2+}]_i$ increase was recorded and superoxide generation was measured using cytochrome c reduction assay. The results are shown FIG. 4. The data of FIG. 4 are presented as means ±S.E. from at least three independent experiments.

Stimulation of neutrophils with the three peptides resulted in an internal calcium increase (FIG. 4A). U937 human promonocytic cells were also activated by three of the peptides (FIG. 4A). All the peptides also enhanced superoxide generation by neutrophils with a similar concentration dependency as observed for the $[Ca^{2+}]_i$ increase in these cells (FIG. 4B). Monocytes and neutrophils were stimulated with 10 µM of each peptide.

Next, the effects of HFYLPM, MFYLPM, and HFYLPm on intracellular calcium release in several non-leukocytic cell lines were examined. NIH3T3 (NIH Swiss mouse embryo fibroblast), 3Y1 (Rat embryonic fibroblast), 3T3L1 (preadipocyte), and PC12 (rat adrenal pheochromocytoma) cells showed no response to the three peptides in terms of $[Ca^{2+}]_i$ rise (FIG. 4A). These results suggest that the effect of the peptides is specific for human leukocytes.

Jurkat human T cell leukemia cells were stimulated by HFYLPM and HFYLPm showing maximal activity at 10 µM and 30 µM peptide concentration each other (FIG. 4A). Meanwhile, MFYLPM did not cause a similar intracellular calcium mobilization in Jurkat cells even upon 30 µM stimulation (FIG. 4A). This suggests that only HFYLPM and HFYLPm but not MFYLPM can bind to receptor(s) on Jurkat T cells. HL60 human promyelocytic cells were also tested for stimulation by the three peptides. As depicted in FIG. 4A, MFYLPM and HFYLPm caused a $[Ca^{2+}]_i$ increase in HL60 cells. In this case, HFYLPM did not evoke an intracellular calcium rise in HL60 cells even after a 20 µM stimulation (FIG. 4A). Thus, HL60 cells seem to specifically respond to MFYLPM and HFYLPm, but not to HFYLPM.

Example 8

Effect of the Peptides on Differentiation Specificity of Cell

Figure 5:
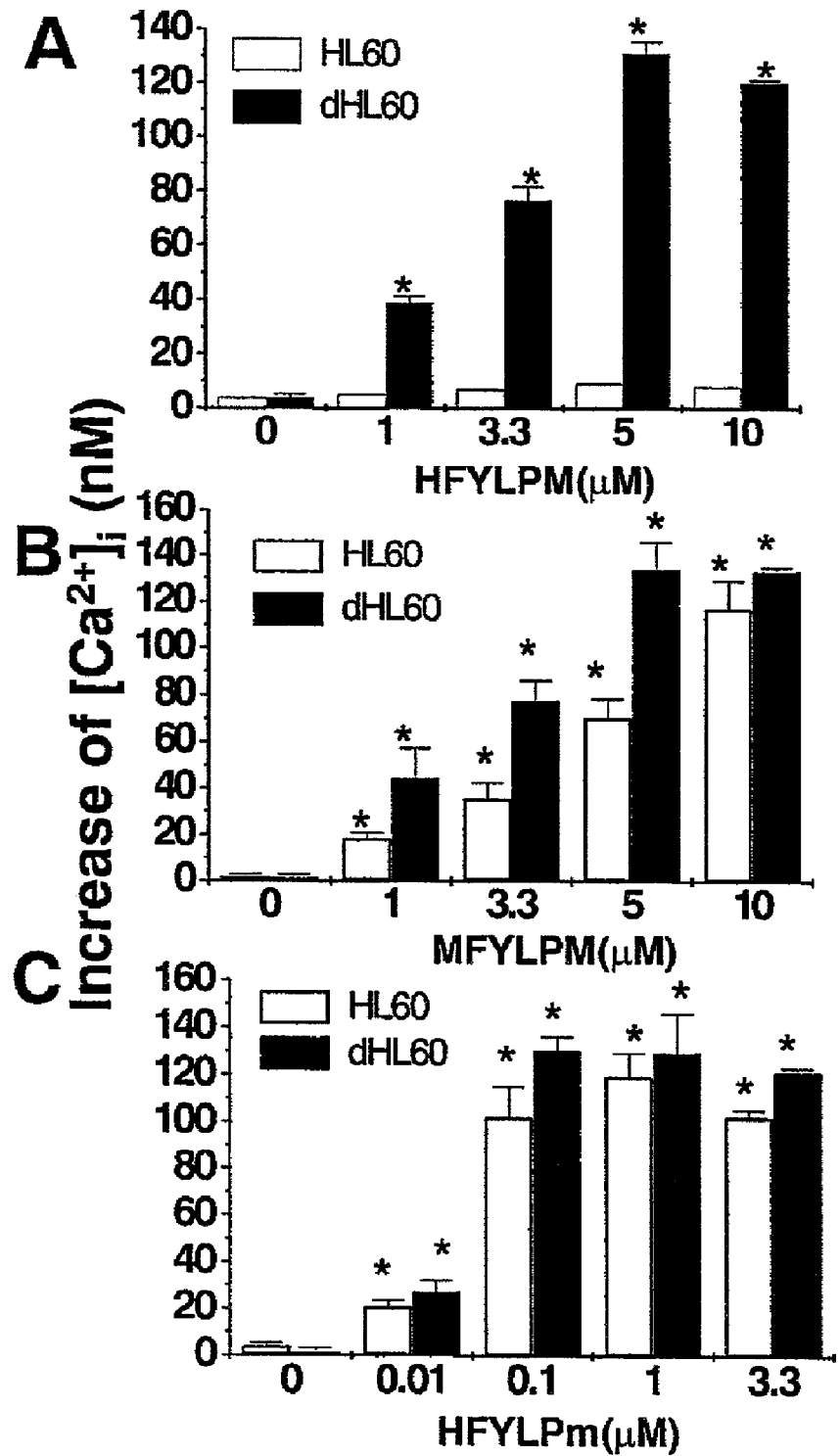
FIG. 5 shows differentiation specificity of various concentrations of peptides HFYLPM (A), MFYLPM (B), and HFYLPm (C)

Although HFYLPM, MFYLPM, and HFYLPm stimulated human neutrophils to increase their $[Ca^{2+}]_i$ and to generate superoxides (FIG. 4), the experimental results indicated that only MFYLPM and HFYLPm, but not HFYLPM, induced an intracellular calcium rise in HL60 human promyelocytic cells (FIG. 4A). A test where the three peptides on HL60 cells that had differentiated into granulocytes after having been cultured in the presence of 1.25% DMSO for 4 days was performed. HL60 cells were cultured in RPMI medium containing 20% FCS. To induce differentiation of the cells into granulocytes, the cells were cultured in the presence of 1.25% DMSO for 4 days. Healthy HL60 and differentiated HL60 cells (dHL60) were loaded with fura-2 and treated with various concentrations of HFYLPM (A), MFYLPM (B), and HFYLPm (C). The peak level of the $[Ca^{2+}]_i$ increase was recorded. Differentiation of the cells into granulocytes was confirmed by monitoring the morphological change and the generation of superoxide upon fMLF treatment as described before (25). The differentiated HL60 cells were stimulated with various concentrations of HFYLPM, MFYLPM, and HFYLPm. The results of differentiation specificity tests of the peptides are shown in FIG. 5. The data of FIG. 5 are means ±S.E. from four independent experiments. *P<0.01 versus vehicle treatment.

As shown in FIG. 5, HFYLPM affected $[Ca^{2+}]_i$ in differentiated but not undifferentiated HL60 cells in a concentration-dependent manner with maximal effect at 5 µM (A). On the contrary, MFYLPM and HFYLPm stimulated both undifferentiated and differentiated HL60 cells resulting in $[Ca^{2+}]_i$ rise (B and C). Stimulation of the differentiated HL60 cells with HFYLPM, MFYLPM, and HFYLPm also resulted in superoxide generation within similar concentrations as required for the $[Ca^{2+}]_i$ increase.

Overall, The above results indicate that HFYLPM, MFYLPM, and HFYLPm are potent stimulators of human phagocytic cells and that HFYLPM affects only differentiated neutrophils and does not affect undifferentiated myelocytes.

Example 9

Effect of fMLF on the novel Peptides-induced $[Ca^{2+}]_i$ increase

Figure 6:
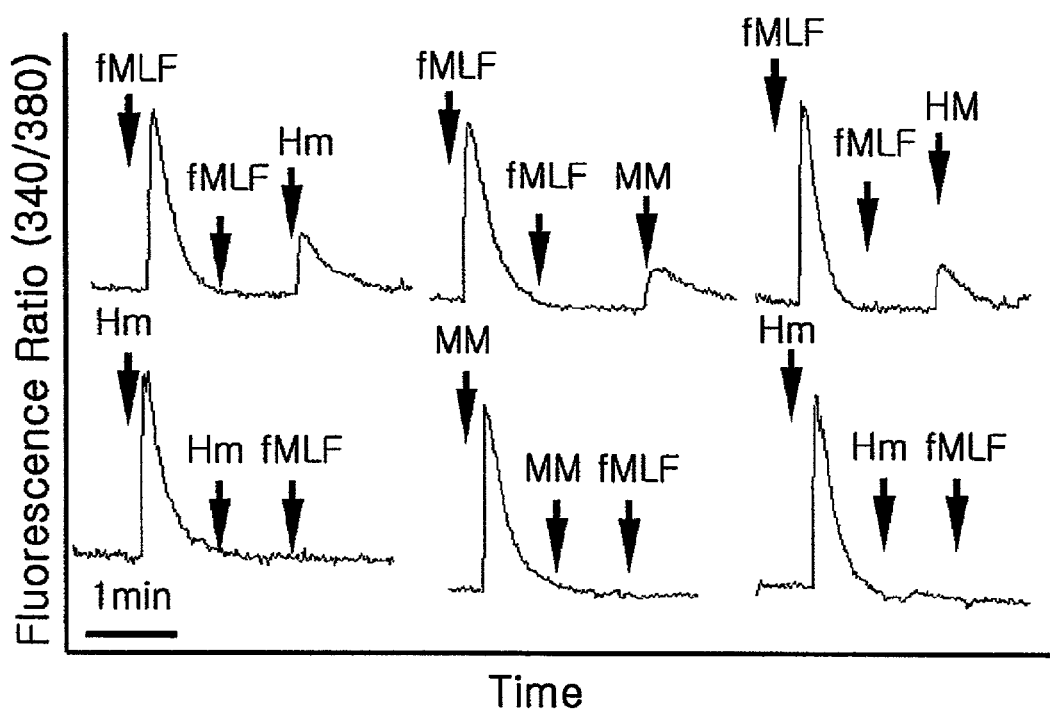
FIG. 6 shows the effect of N-formyl-methionyl-leucyl-phenylalanine (fMLF) on the peptide-induced $[Ca^{2+}]_i$ increase.

Among various agonists, fMLF is known to cause superoxide production and $[Ca^{2+}]_i$ increase in phagocytic cells by binding to its specific receptor (7). To check whether the novel peptides can cross-desensitize the signaling by fMLF, the effect of fMLF on the novel peptides-induced $[Ca^{2+}]_i$ increase and vice versa was examined. FIG. 6 shows the measurement results. The results of FIG. 6 shown are from one experiment that is representative of at least three independent experiments.

In FIG. 6, "Hm" means HFYLPm, "HM" means HFYLPM, and "MM" means MFYLPM. The concentrations used were 1 μM (HFYLPm and fMLF) and 10 μM (HFYLPM and MFYLPM). 340 nm/380 mn ratios in fluorescence were monitored on fura-2-loaded differentiated HL60 cells before and during sequential addition of agonists at the times indicated by the arrows. Fura-2-loaded differentiated HL60 cells were stimulated with a peptide, and complete desensitization of its corresponding receptor was confirmed by the fact that any additional $[Ca^{2+}]_i$ increase was not observed upon the subsequent stimulation with the same peptide. However, considerable responses were shown by the stimulation with saturating concentrations of three novel peptides following the treatment with a saturating concentration of fMLF (upper part of FIG. 6). Conversely, a saturating concentration of one of three novel peptides could completely block the calcium response to a following stimulation with a saturating concentration of fMLF (below part of FIG. 6). These results suggest that the novel peptides can cross-desensitize fMLF signaling, and that novel peptides can also bind an additional receptor other than the fMLF receptor in the cells.

Example 10

Chemotactic Effect of Peptides

Chemotaxis assays of the peptide were performed using multiwell chambers (Neuroprobe Inc., Gaithersburg, Md.) (20). Briefly, the prepared isolated human monocytes were suspended in RPMI at a concentration of 1×10⁶ cells/ml of serum-free RPMI, and 25 □ of the suspension were placed onto the upper well of a 96-well chemotaxis chamber that was separated by a polyhydrocarbon filter with a 5 □ pore size (3 □ diameter pores not coated with polyvinylpyrrolidone for neutrophils) from peptides or an fMLF-containing lower well. After incubation for 2 hours (90 minutes for neutrophils) at 37° C., non-migrated cells were removed by scraping them out, and cells that migrated across the filter were dehydrated, fixed, and stained with hematoxylin (Sigma, St. Louis, Mo.). The stained cells in five randomly chosen high power fields (HPF) (400×) in that well were then counted (21). The numbers of migrated cells were determined by counting them in a high power field (400×). For a checkboard analysis, cells were re-suspended in RPMI containing various concentrations of the peptide just before transferring them to the upper wells as described before (22).

Figure 7:
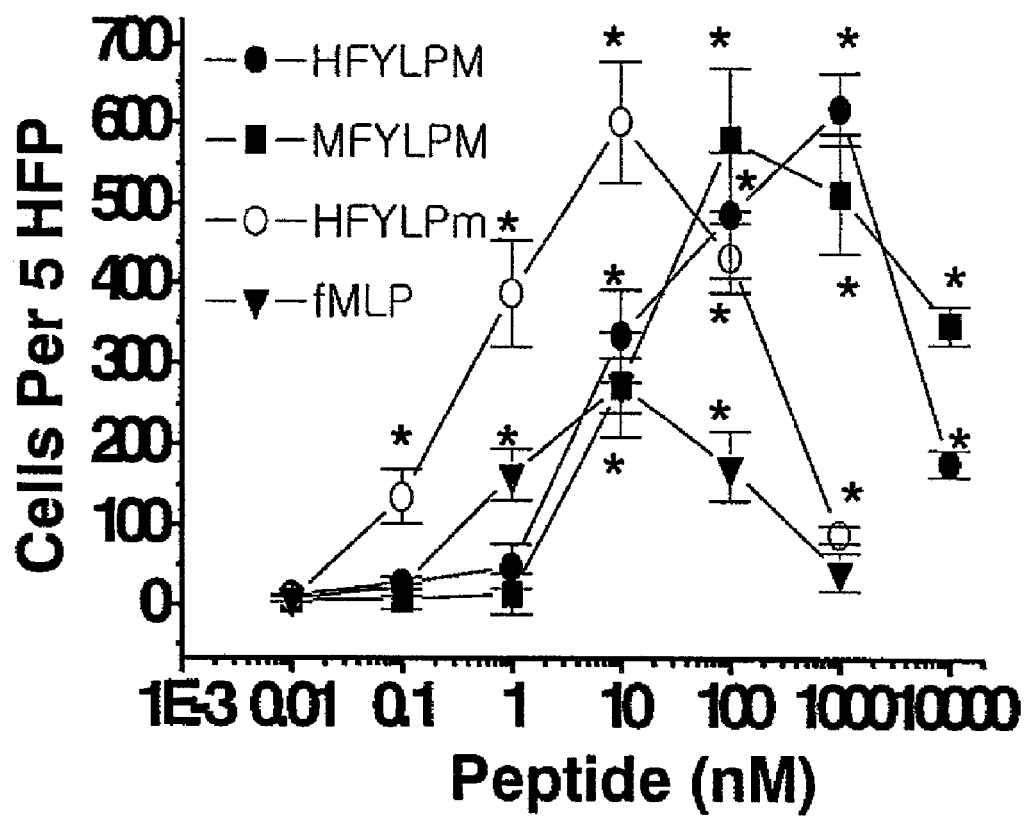
FIG. 7 shows chemotactic effect of the novel peptides of the present invention for human phagocytes.

A test for determining that the novel peptides stimulate superoxide generation and $[Ca^{2+}]_i$ increase in human phagocytic cells was performed. These peptide-induced phagocyte activation phenomena are similar to chemoattractant-induced ones. Therefore, it was checked whether the peptides exhibited chemotactic activity on the cells. The test results are shown FIG. 7. The data of FIG. 7 are presented as means±S.E. of three independent experiments, each performed in duplicate. *P<0.01 versus vehicle treatment.

HFYLPM, MFYLPM, and HFYLPm induced migration of human monocytes within a 0.01 to 10 μM (0.001 to 1 μM for HFYLPm) concentration, showing a bell-shaped concentration response curve in human monocytes similar to the fMLF-induced one as reported previously (34). The maximal cellular migration-inducing activity mediated by the peptides was over 200% of that of a 100 nM fMLF-induced one (FIG. 7). The three peptides also induced cellular migration in human neutrophil within similar concentrations as for monocyte migration. In three experiments with independently prepared leukocytes, the peptides showed cellular migration-inducing activity with similar patterns.

To distinguish whether the peptide-induced monocyte migration is chemotaxis or chemokinesis, a checkboard analysis was performed as described above (22, 26). The analysis results are shown in Table 1.

TABLE 1

Checkboard analysis of monocyte migration across polycarbonate membrane after treatment with HFYLPM, MFYLPM, and HFYLPm[a].

| HFYLPM | HFYLPM Above (nM) | | | |
|---|---|---|---|---|
| Below (nM) | 0 | 10 | 100 | 1000 |
| 0 | 10.5 ± 3.42 | 11.0 ± 2.54 | 13.3 ± 2.40 | 10.0 ± 2.57 |
| 10 | 312 ± 23.0 | 47.7 ± 7.43 | 14.0 ± 3.97 | 10.7 ± 2.21 |
| 100 | 494 ± 34.0 | 366 ± 26.1 | 54.0 ± 14.5 | 19.3 ± 11.4 |
| 1000 | 612 ± 66.7 | 505 ± 53.7 | 210 ± 45.6 | 62.3 ± 21.0 |
| MFYLPM | MFYLPM Above (nM) | | | |
| Below (nM) | 0 | 10 | 100 | 1000 |
| 0 | 16.3 ± 4.51 | 11.3 ± 2.42 | 15.0 ± 3.50 | 11.0 ± 2.67 |
| 10 | 198 ± 32.3 | 33.7 ± 8.93 | 16.0 ± 3.16 | 12.3 ± 3.43 |
| 100 | 557 ± 29.5 | 425 ± 48.3 | 66.3 ± 14.9 | 18.0 ± 4.05 |
| 1000 | 484 ± 43.6 | 395 ± 38.5 | 198 ± 26.7 | 76.7 ± 18.9 |
| HFYLPm | HFYLPm Above (nM) | | | |
| Below (nM) | 0 | 10 | 100 | 1000 |
| 0 | 16.3 ± 3.22 | 11.3 ± 3.20 | 15.0 ± 4.82 | 11.0 ± 2.33 |
| 10 | 313 ± 32.4 | 53.7 ± 12.4 | 20.0 ± 5.56 | 12.3 ± 7.91 |
| 100 | 527 ± 29.5 | 325 ± 28.4 | 56.3 ± 9.37 | 28.0 ± 8.06 |
| 1000 | 425 ± 74.0 | 295 ± 56.6 | 98.3 ± 26.9 | 76.7 ± 17.8 |

Note)
[a]Monocyte migration was analyzed for 2 hr across a polycarbonate membrane with a 5 □ pore size. Various concentrations of HFYLPM, MFYLPM, and HFYLPm were placed in the upper and lower compartments of the chambers. Data are presented as means ± SE for migrated monocytes in 5 HPF counted in triplicate of two independent experiments.

As shown in Table 1, a gradually increasing concentration gradient of each n the lower chamber and upper chamber induced significant migration of he peptides. This implies that the three peptides induce chemotaxis in human monocytes.

Example 11

Effect of PTX on the Peptides-induced Chemotatic Migration in Monocytes

Figure 8:
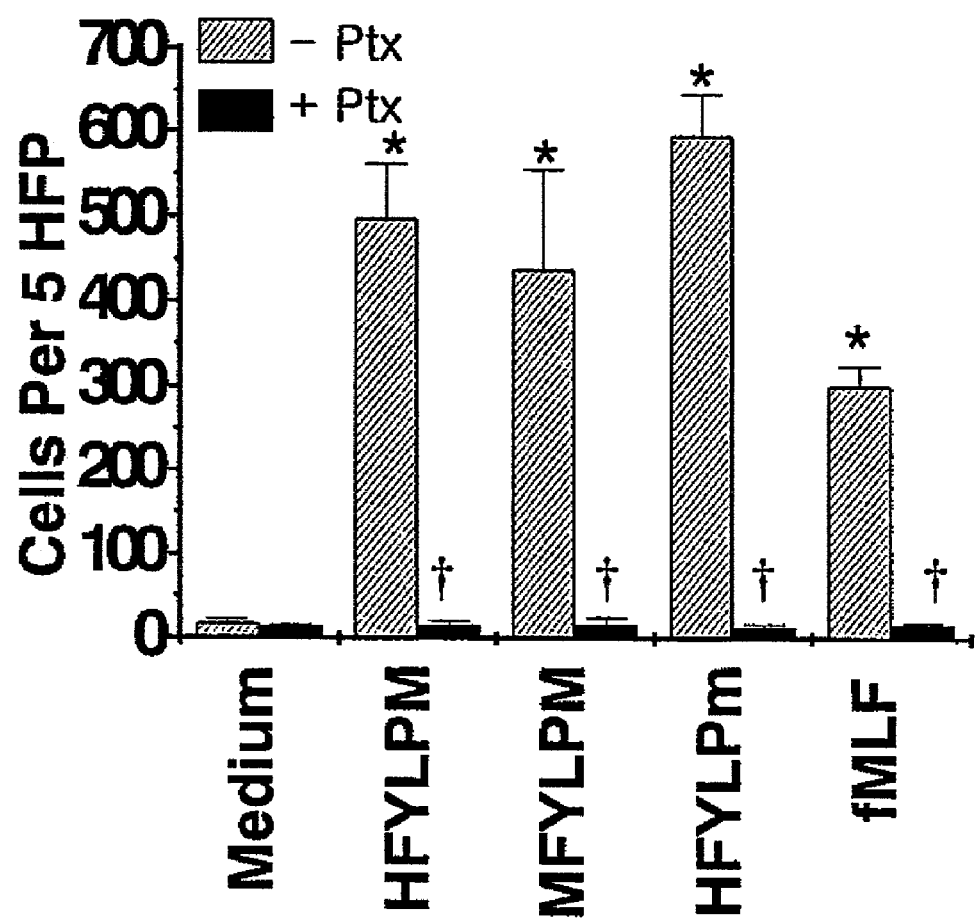
FIG. 8 shows the effect of PTX on the peptides (HFYLPM (SEQ ID NO: 1), MFYLPM (SEQ ID NO: 2), and HFYLPm (SEQ ID NO: 3))-induced chemotactic migration in monocytes.

Several extracellular signals including many chemoattractants activate phagocytic cells via pertussis toxin (PTX)-sensitive G-protein(s) (27-29). Therefore, the involvement of PTX-sensitive G-protein(s) on the peptide-induced monocyte activation was examined. Monocytes were preincubated with PTX (1 □/ml) or vehicle only for 90 minutes at 37° C. The cells were used for chemotaxis assay with HFYLPM (1 μM), MFYLPM (1 μM), HFYLPm (100 nM), and fMLF (100 nM). The numbers of migrated cells were determined by counting them in a high power field (400×). The results are illustrated in FIG. 8. The data of FIG. 8 are presented as means±S.E. of two independent experiments each performed in duplicate. *P<0.01 versus medium treatment and †P<0.01 versus peptide treatment, respectively.

As shown in FIG. 8, preincubation of monocytes with PTX (1 □/ml) for 90 minutes led to complete inhibition of the HFYLPM, MFYLPM, and HFYLPm-induced monocyte chemotaxis. Under the same condition, monocyte chemotaxis induced by fMLF, a well-known chemoattractant, was also completely blocked. These results, therefore, imply that HFYLPM, MFYLPM, and HFYLPm stimulate human monocytes via PTX-sensitive G-protein(s).

Example 12

Receptor-specificity of the Three Peptides

Figure 9:
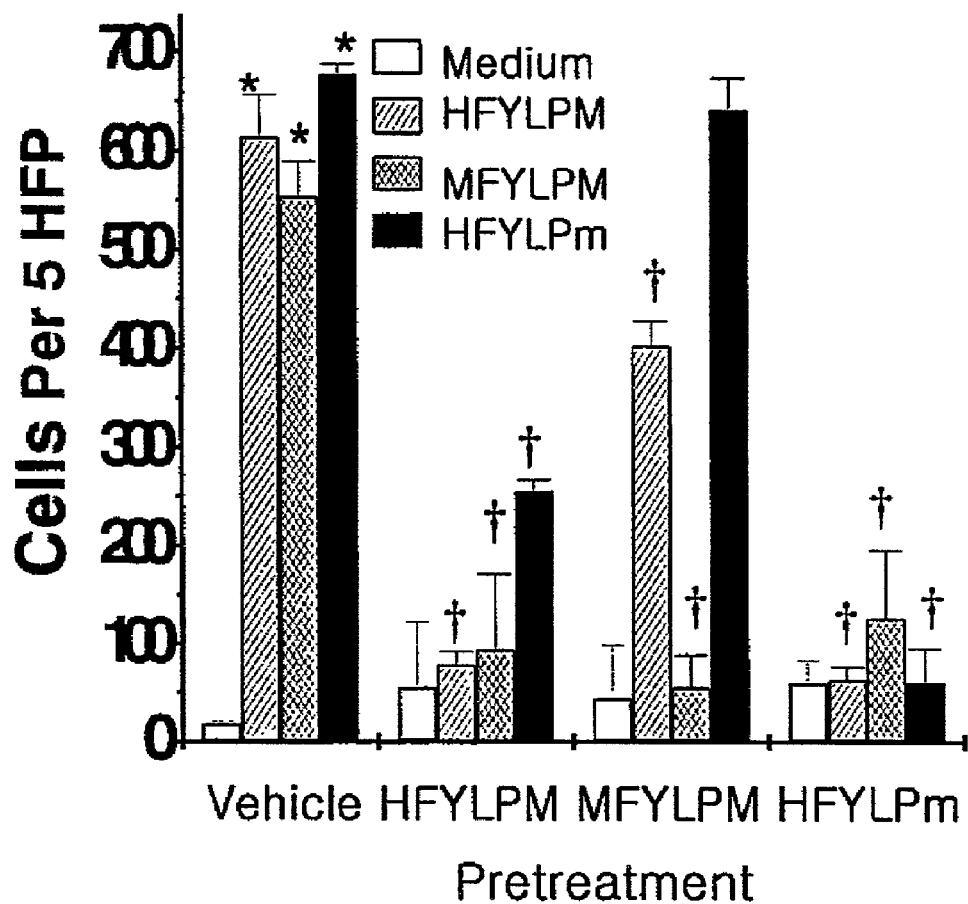
FIG. 9 shows specificity of peptides (HFYLPM (SEQ ID NO: 1), MFYLPM (SEQ ID NO: 2), and HFYLPm (SEQ ID NO: 3))-induced monocyte chemotaxis.

The three peptides, HFYLPM, MFYLPM, and HFYLPm which have similar sequences, exerted similar effects on human leukocytes in that they stimulated superoxide generation and chemotactic migration involving PTX-sensitive G-protein(s). So an attempt to reveal whether the three peptides acted through the same or different receptor(s) was carried out. For this purpose, monocytes were preincubated with 10 μM of each peptide, HFYLPM, MFYLPM, or HFYLPm for 10 minutes at 37° C., or they remained untreated. After washing twice, the cells were used for chemotaxis assay. The cells were allowed to migrate towards the maximal effective concentrations of each peptide (1 μM HFYLPM, 1 μM MFYLPM, or 10 nM HFYLPm) or medium. After fixing and staining of the membrane, migrated cells were quantified microscopically. The results are shown in FIG. 9. The data of FIG. 9 are presented as means±S.E. of three independent experiments each performed in duplicate. *P<0.01 versus medium treatment and †P<0.01 versus peptide treatment, respectively.

As shown in FIG. 9, preincubation of the cells with one peptide caused complete inhibition of the same peptide-induced cell migration, indicating homologous receptor down-regulation. When the cells were preincubated with HFYLPM, MFYLPM- or HFYLPm-induced cell migration was completely or partially inhibited. Pretreatment of MFYLPM caused partial inhibition of HFYLPM-induced chemotaxis and no inhibition of HFYLPm-induced one. Pretreatment of HFYLPm caused almost complete inhibition of all the peptides-induced chemotactic migration of monocytes.

Example 13

Comparison of the Signaling of the Peptides in Inducing Chemotaxis

Monocytes were pretreated either with LY (LY294002, 50 μM), GFX (GF109203X, 5 μM), or PD (PD98059, 50 μM), or they remained untreated for the control After an incubation of the indicated periods (15 minutes for LY294002 and GF109203X, 60 minutes for PD98059), the cells were washed twice and used for chemotaxis assay. 25 □ of monocytes at 1×10$^6$ cells/ml were added to the upper wells and allowed to migrate for 2 hrs at 37° C. (humidified atmosphere; 5% $CO_2$) toward each peptide (1 μM HFYLPM, 1 μM MFYLPM, or 10 nM HFYLPm) or medium. After fixing and staining of the membrane, the numbers of migrated cells were determined by counting them in a high power field (400×). The results are shown FIG. 10. The data are presented as means ±S.E. of three independent experiments each performed in duplicate. *P<0.01 versus medium treatment and †P<0.01 versus peptide treatment, respectively.

Figure 10:
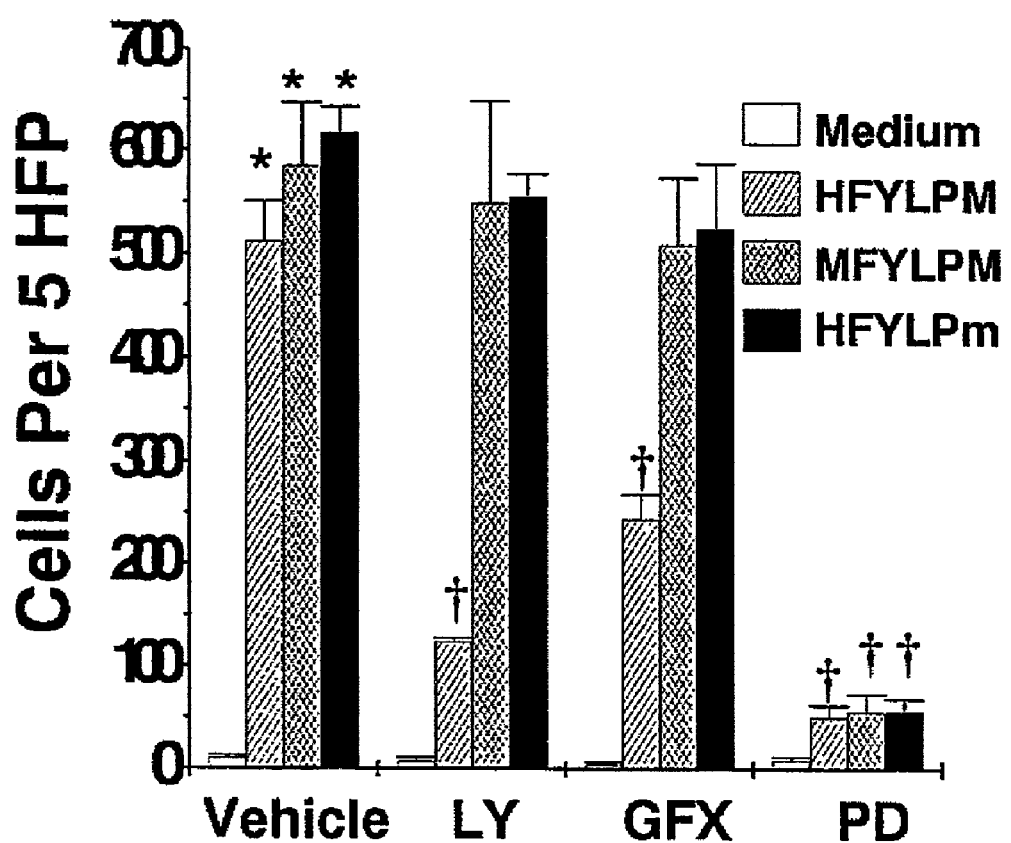
FIG. 10 shows the effect of enzyme inhibitors on monocyte chemotaxis induced by the peptides of the present invention.

As shown in FIG. 10, P13-kinase inhibitor (LY294002) and PKC inhibitor (GF109203X) inhibited HFYLPM-induced chemotaxis about 75% and 50%, respectively, but the inhibitors had no effect on MFYLPM- and HFYLPm-induced chemotaxis. These results indicate that HFYLPM, but not MFYLPM and HFYLPm, induce monocyte chemotaxis via P13-kinase and PKC activation. Pretreatment of the cells with MEK inhibitor (PD98059) caused almost complete inhibition of each peptide-induced chemotaxis. This implies that MEK activation is a critical event for chemotaxis induced by the three peptides.

In the above experiments investigating cell specificity of the peptides, the fact that the three peptides, HFYLPM, MFYLPM, and HFYLPm affected only human leukocytic cells including phagocytes and Jurkat T cells was observed. Non-leukocytic cells such as fibroblasts and neuronal cells were not affected by the novel peptides (FIG. 4A). Among human leukocytes, Jurkat T cells were stimulated only by HFYLPM and HFYLPm, but not by MFYLPM (FIG. 4A). However, undifferentiated HL60 cells were activated only by MFYLPM and HFYLPm, but not by HFYLPM (FIG. 4A). It is surprising that just one amino acid change would create cell specificity, differentiating between different leukocytic cells, such as Jurkat T cells and HL60 promyelocytic cells. The specificity for Jurkat T cells versus undifferentiated HL60 cells resides in the 1st residue (H versus M) of the hexapeptide containing the consensus sequence (XFYLPM). The fact that HL60 cells were stimulated by HFYLPm but not by HFYLPM suggests that the two peptides have different receptor-specificity and that at least one certain receptor specific for HFYLPm exists on HL60 cells. Although MFYLPM and HFYLPm acted on undifferentiated HL60 and HL60 cells differentiated into granulocytes, HFYLPM acted exclusively on differentiated HL60 cells. These results suggest that an unidentified receptor(s) for HFYLPM might exist on the differentiated HL60 cells, but that it is not present on the undifferentiated cells. The differentiation of HL60 cells into granulocytes is accompanied by several expression pattern changes for various proteins (30-32). For instance, the fMLF receptor is not expressed on undifferentiated HL60 cells (33). However, HL60 cells differentiated into granulocytes do express a functional receptor for fMLF that plays an important role in the defense against invading pathogens (34). Although both the fMLF-receptor(s) and the HFYLPM-receptor(s) are restricted to differentiated HL60 cells, HFYLPM-receptor(s) but not fMLF-receptor(s) are expressed on Jurkat T cells (35). This indicates that HFYLPM can bind to receptors that are distinct from fMLF-receptor(s).

The novel peptides identified in the present invention, HFYLPM, MFYLPM, and HFYLPm induced intracellular calcium mobilization, superoxide generation, and chemotactic activity for human phagocytic cells (FIGS. 2, 3 and, 7). HFYLPM and MFYLPM stimulate monocytes in a concentration range of 0.001 to 10 μLM (0.33 μM to 10 μM for superoxide production; 0.01 to 1 μM for $[Ca^{2+}]_i$ release; 0.001 to 1 μM for chemotaxis). HFYLPm is more potent than two of the peptides stimulating the cells within 0.01 to 100 nM (1 to 100 nM for superoxide generation; 0.1 to 100 nM for $[Ca^{2+}]_i$ release; 0.001 to 10 nM for chemotaxis). Through checkboard analysis, it is confirmed that the peptide-induced activities are chemotaxis rather than chemokinesis (Table 1). Previous reports demonstrated that many leukocyte chemoattractants such as fMLF and various chemokines activate leukocytes via PTX-sensitive G-protein-coupled receptors and phospholipase C β resulting in cellular responses such as $[Ca^{2+}]_i$ rise, superoxide generation, and chemotaxis of the cells (25, 36). Based on these circumstances, the fact that three novel peptides, HFYLPM, MFYLPM, and HFYLPm can act as chemoattractants for human phagocytic cells can be suggested.

Pretreatment of the cells with effective concentrations of HFYLPM, MFYLPM, or HFYLPm for 10 minutes caused complete inhibition of the same peptide-induced cell migration, indicating homologous receptor down-regulation (FIG. 9). When the cells were preincubated with HFYLPM or HFYLPm for 10 minutes, it led to almost complete inhibition of MFYLPM-induced migration of monocytes (FIG. 9). However, pretreatment of the cells with MFYLPM only partially or never affected HFYLPM- or HFYLPm-induced monocyte migration, respectively (FIG. 9). These results suggest that HFYLPM and HFYLPm may have at least one unique and independent receptor for MFYLPM on monocytes.

Through the study of the intracellular signaling pathways by the three peptides, the fact that the HFYLPM-induced migration, but not the MFYLPM- and HFYLPm-induced migration, is sensitive to LY294002 and GF109203X indicating PI3-kinase- and PKC-dependent (FIG. 10) participation was found. However, all three peptides-induced migrations are sensitive to PD98059 implying that MEK activity is critical for the migration. These results suggest that the peptide HFYLPM may bind distinct receptors for MFYLPM and HFYLPm. And the receptor that HFYLPM binds would be coupled to PI3-kinase and PKC in monocytes. It is very surprising that peptides sharing essentially the same sequence and differing in stereo specificity by only one amino acid can bind some distinct receptor and induce distinct intracellular signaling.

Specific ligands act via specific receptors. This specificity results from a combination of subtle conformational and amino acid sequence differences. As described above, a synthetic hexapeptide, Trp-Lys-Tyr-Met-Val-D-Met-$CONH_2$ (WKYMVm), stimulates several human leukocytes except T cells (15, 24, 37, 38). Recently Le et al. reported that the WKYMVm peptide acts at two fMLF receptor subtypes (39). Although HFYLPM and HFYLPm have an effect similar to WKYMVm on human phagocytic cells, they additionally exhibit specificity for Jurkat T cells. In the previous report of the present inventor, the fact that the Y in the 3rd position of the hexapeptide and the M in the 6th position were important for the activity of WKYMVm on phosphoinositide hydrolysis in human leukocytes (24) was demonstrated. The new peptides (HFYLPM SEQ ID NO. 1, MFYLPM SEQ ID NO. 2, and HFYLPm SEQ ID NO. 3) also have a Y and an M in the 3rd and the 6th position of the hexapeptide (FIG. 2). Remembering that WKYMVm was modified from the lead sequence (MIW)KYM(PN)M (15, 24), it is suggested that, while Y at the 3rd, P or V at the 5th, and M at the 6th position of the hexapeptide are important for the binding to a certain type of receptor, the 1st residue of the hexapeptide can determine the specificity of the peptide for receptor.

It seems reasonable to suggest that there might be a pool of receptors for a certain group of chemoattractants including novel peptides of the present invention on the leukocyte surface. Each leukocytic cell may have a distinct expression profile. The results that Jurkat cells were stimulated by HFYLPM and HFYLPm but not by MFYLPM, while HL60 cells were stimulated by HFYLPm and MFYLPM but not by HFYLPM, support the notion described above. Each peptide among three novel chemotactic peptides may bind to some of the receptors. Some receptors can be occupied by more than two peptides and some can be occupied by only one. Based on the observations above: 1) the three peptides have different cell type specificities among leukocytes, 2) MFYLPM-induced monocyte chemotaxis could be inhibited by the other two peptides but not vice versa, 3) the HFYLPM-induced cell migration was mediated by a different signaling than MFYLPM and HFYLPm, it can be suggested that the three novel peptides act on some shared and some distinct receptors on a certain group in leukocytes.

Since HFYLPM, MFYLPM, and HFYLPm were identified by screening artificially synthesized peptides and one peptide was modified, it is guessed that these peptides can be mimetic of some natural ligands. Sequence similarities between the novel peptides and known proteins searching the databases (SWISS-PROT and TrEMBL) were investigated. A protein carrying the exact same sequence as the peptides was not found, however, several viral proteins such as the major capsid protein of the pseudorabies virus contain the X(F/K)Y(L/M)(V/P)M sequence were found. There is sequence homology between novel peptides of the present invention and the viral protein.

Although various chemokines and chemoattractants have been identified, few short peptides acting on human leukocytes have been known until now. WKYMVm (15, 24, 37, 38) and fMLF (32-34, 40) have been useful tools for studying phagocyte activation. Since the novel peptides HFYLPM, MFYLPM, and HFYLPm stimulate human phagocytes including monocytes and neutrophils (FIG. 4A), these three peptides can also be used as tools to study phagocyte signaling. In the area of T cell activation and signaling, there has been no report yet on small peptides acting on T cells. Since two of the novel peptides, HFYLPM and HFYLPm, stimulate Jurkat T cells inducing $[Ca^{2+}]_i$ rise, they can serve as a tool to characterize T cell activation.

REFERENCES

1. Bokoch GM. Chemoattractant signaling and leukocyte activation. Blood. 1995;86:1649-1660.
2. Rossi F. The O2—forming NADPH oxidase of the phagocytes: nature, mechanisms of activation and function. Biochim Biophys Acta. 1986;853:65-89.
3. Segal AW, Abo A. The biochemical basis of the NADPH oxidase of phagocytes. Trends Biochem Sci. 1993;18:43-47.
4. Williams LM, Ridley A J. Lipopolysaccharide induces actin reorganization and tyrosine phosphorylation of Pyk2 and paxillin in monocytes and macrophages. J Immunol. 2000;164:2028-2036.
5. Pound JD, Lund J, Jefferis R. Human Fc gamma RI triggering of the mononuclear phagocyte respiratory burst. Mol Immunol. 1993;30:469-478.
6. Su SB, Gong W, Gao JL, et al. A seven-transmembrane, G protein-coupled receptor, FPRL1, mediates the chemotactic activity of serum amyloid A for human phagocytic cells. J Exp Med. 1999;189:395-402.
7. Rane MJ, Carrithers SL, Arthur JM, Klein JB, McLeish KR. Formyl peptide receptors are coupled to multiple mitogen-activated protein kinase cascades by distinct signal transduction pathways: role in activation of reduced nicotinamide adenine dinucleotide oxidase. J Immunol. 1997; 159:5070-5078.
8. Prieschl EE, Kulmburg PA, Baumruker T. The nomenclature of chemokines. Int Arch Allergy Immunol. 1995;107: 475-483.
9. Baggiolini M, Dewald B, Moser B. Interleukin-8 and related chemotactic cytokines—CXC and CC chemokines. Adv Immunol. 1994;55:97-179.
10. Houghten RA, Pinilla C, Blondelle SE, Appel JR, Dooley CT, Cuervo JH. Generation and use of synthetic peptide combinatorial libraries for basic research and drug discovery. Nature. 1991;354:84-86.
11. Owens RA, Gesellchen PD, Houchins BJ, DiMarchi RD. The rapid identification of HIV protease inhibitors through the synthesis and screening of defined peptide mixtures. Biochem Biophys Res Commun. 1991;181:402-408.

12. Hayashi S, Kurdowska A, Miller EJ, Albright ME, Girten BE, Cohen AB. Synthetic hexa- and heptapeptides that inhibit IL-8 from binding to and activating human blood neutrophils. J Immunol. 1995;154:814-824.
13. Aramburu J, Yaffe MB, Lopez-Rodriguez C, Cantley LC, Hogan PG, Rao A. Affinity-driven peptide selection of an NFAT inhibitor more selective than cyclosporin A. Science. 1999;285:2129-2133.
14. Dooley CT, Ny P, Bidlack JM, Houghten RA. Selective ligands for the mu, delta, and kappa opioid receptors identified from a single mixture based tetrapeptide positional scanning combinatorial library. J Biol Chem. 1998;273: 18848-18856.
15. Baek SH, Seo JK, Chae CB, Suh PG, Ryu SH. Identification of the peptides that stimulate the phosphoinositide hydrolysis in lymphocyte cell lines from peptide libraries. J Biol Chem. 1996;271:8170-8175.
16. Kavelaars A, Broeke D, Jeurissen F, et al. Activation of human monocytes via a non-neurokinin substance P receptor that is coupled to Gi protein, calcium, phospholipase D, MAP kinase, and IL-6 production. J Immunol. 1994;153: 3691-3699.
17. Ottonello L, Tortolina G, Amelotti M, Dallegri F. Soluble Fas ligand is chemotactic for human neutrophilic polymorphonuclear leukocytes. J Immunol. 1999;162:3601-3606.
18. Itoh K, Okubo K, Utiyama H, Hirano T, Yoshii J, Matsubara K. Expression profile of active genes in granulocytes. Blood. 1998;92:1432-1441.
19. Park J Y, Kim I J, Lee M H, et al. Identification of the peptides that inhibit the stimulation of thyrotropin receptor by Graves' immunoglobulin G from peptide libraries. Endocrinology. 1997;138:617-626.
20. Burnham D N, Uhlinger D J, Lambeth J D. Diradylglycerol synergizes with an anionic amphiphile to activate superoxide generation and phosphorylation of p47phox in a cell-free system from human neutrophils. J Biol Chem. 1990;265:17550-17559.
21. Grynkiewicz G, Poenie M, Tsien R Y. A new generation of Ca2+ indicators with greatly improved fluorescence properties. J Biol Chem. 1985;260:3440-3450.
22. Dunzendorfer S, Schratzberger P, Reinisch N, Kahler C M, Wiedermann C J. Secretoneurin, a novel neuropeptide, is a potent chemoattractant for human eosinophils. Blood. 1998;91:1527-1532.
23. Tenscher K, Metzner B, Schopf E, Norgauer J, Czech W. Recombinant human eotaxin induces oxygen radical production, Ca(2+)-mobilization, actin reorganization, and CD11b upregulation in human eosinophils via a pertussis toxin-sensitive heterotrimeric guanine nucleotide-binding protein. Blood. 1996;88:3195-3199.
24. Seo J K, Choi S Y, Kim Y, et al. A peptide with unique receptor specificity: stimulation of phosphoinositide hydrolysis and induction of superoxide generation in human neutrophils. J Immunol. 1997;158:1895-1901.
25. Korchak H M, Rossi M W, Kilpatrick L E. Selective role for beta-protein kinase C in signaling for 0-2 generation but not degranulation or adherence in differentiated HL60 cells. J Biol Chem. 1998;273:27292-27299.
26. Syrovets T, Thillet J, Chapman M J, Simmet T. Lipoprotein(a) is a potent chemoattractant for human peripheral monocytes. Blood. 1997;90:2027-2036.
27. Tanabe S, Heesen M, Yoshizawa I, et al. Functional expression of the CXC-chemokine receptor-4/fusin on mouse microglial cells and astrocytes. J. Immunol. 1997; 159:905-911.
28. Badolato R, Johnston J A, Wang J M, et al. Serum amyloid A induces calcium mobilization and chemotaxis of human monocytes by activating a pertussis toxin-sensitive signaling pathway. J. Immunol. 1995;155:4004-4010.
29. Teixeira M M, Giembycz M A, Lindsay M A, Hellewell P G. Pertussis toxin shows distinct early signalling events in platelet-activating factor-, leukotriene B4-, and C5a-induced eosinophil homotypic aggregation in vitro and recruitment in vivo. Blood. 1997;89:4566-4573.
30. Nakashima S, Iwasaki Y, Mizutani T, et al. Differential expression of protein kinase C isozymes and small GTP-binding proteins during HL60 cell differentiation by retinoic acid and cyclic AMP: relation with phospholipase D (PLD) activation. Immunobiology. 1996-1997;196:588-598.
31. Fuchs A, Bouin A P, Rabilloud T, Vignais P V. The 40-kDa component of the phagocyte NADPH oxidase (p40phox) is phosphorylated during activation in differentiated HL60 cells. Eur J Biochem. 1997;249:531-539.
32. Sham R L, Phatak P D, Belanger K A, Packman C H. Functional properties of HL60 cells matured with all-trans-retinoic acid and DMSO: differences in response to interleukin-8 and fMLP. Leuk Res. 1995;19:1-6.
33. Prossnitz E R, Quehenberger O, Cochrane C G, Ye R D. Signal transducing properties of the N-formyl peptide receptor expressed in undifferentiated HL60 cells. J Immunol. 1993; 151: 5704-5715.
34. Montero M, Garcia-Sancho J, Alvarez J. Activation by chemotactic peptide of a receptor-operated Ca2+ entry pathway in differentiated HL60 cells. J Biol Chem. 1994; 269:29451-29456.
35. Campbell J J, Qin S, Bacon K B, Mackay C R, Butcher E C. Biology of chemokine and classical chemoattractant receptors: differential requirements for adhesion-triggering versus chemotactic responses in lymphoid cells. J Cell Biol. 1996;134:255-266.
36. Ali H, Sozzani S, Fisher I, et al. Differential regulation of formyl peptide and platelet-activating factor receptors. Role of phospholipase Cbeta3 phosphorylation by protein kinase A. J Biol Chem. 1998;273:11012-11016.
37. Bae Y S, Ju S A, Kim J Y, et al. Trp-Lys-Tyr-Met-Val-D-Met stimulates superoxide generation and killing of *Staphylococcus aureus* via phospholipase D activation in human monocytes. J Leukoc Biol. 1999;65:241-248.
38. Bae Y S, Kim Y, Kim Y, Kim J H, Suh P G, Ryu S H. Trp-Lys-Tyr-Met-Val-D-Met is a chemoattractant for human phagocytic cells. J Leukoc Biol. 1999;66:915-922.
39. Le Y, Gong W, Li B, et al. Utilization of two seven-transmembrane, G protein-coupled receptors, formyl peptide receptor-like 1 and formyl peptide receptor, by the synthetic hexapeptide WKYMVm for human phagocyte activation. J Immunol. 1999;163:6777-6784.
40. Pan Z K, Chen L Y, Cochrane C G, Zuraw B L. fMet-Leu-Phe stimulates proinflammatory cytokine gene expression in human peripheral blood monocytes: the role of phosphatidylinositol 3-kinase. J Immunol. 2000;164:404-411.

What is claimed is:

1. An isolated peptide consisting of an amino acid sequence selected from the group consisting of SEQ ID NO: 1 and SEQ ID NO: 3.

2. The isolated peptide according to claim 1 wherein the peptide activates leukocytes and is in an isolated and substantially pure form.

3. The isolated peptide according to claim 1 which induces superoxide generation by human monocytes and neutrophils.

4. The isolated peptide according to claim 1 which induces intracellular calcium increase by human peripheral blood monocytes and neutrophils.

5. The isolated peptide according to claim 1 which induces intracellular calcium increase by U937, HL-60, differentiated HL-60, and Jurkat cells.

6. The isolated peptide according to claim 1 which induces chemotactic migration of human monocytes and neutrophils in vitro.

7. The isolated peptide according to claim 1 which desensitizes fMLP-induced intracellular calcium increase.

8. A composition comprising a peptide consisting of the amino acid sequence selected from the group consisting of SEQ ID NO: 1 and SEQ ID NO: 3.

* * * * *

SEQUENCE LISTING

<160> NUMBER OF SEQ ID NOS: 32

<210> SEQ ID NO 1
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 1

His Phe Tyr Leu Pro Met
1               5

<210> SEQ ID NO 2
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 2

Met Phe Tyr Leu Pro Met
1               5

<210> SEQ ID NO 3
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Met
<220> FEATURE:
<221> NAME/KEY: SITE
<222> LOCATION: (6)
<223> OTHER INFORMATION: Methionine residue optionally substituted
      with -NH2 group on carboxyl group and D-type

<400> SEQUENCE: 3

His Phe Tyr Leu Pro Met
1               5

<210> SEQ ID NO 4
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 4

Met Phe Tyr Leu Pro Gly
1               5

```
<210> SEQ ID NO 5
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 5

Met Phe Tyr Leu Pro Asp
1               5

<210> SEQ ID NO 6
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 6

His Phe Tyr Leu Pro Gly
1               5

<210> SEQ ID NO 7
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 7

His Phe Tyr Leu Pro Asp
1               5

<210> SEQ ID NO 8
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 8

Met Phe Tyr Leu Val Gly
1               5

<210> SEQ ID NO 9
<211> LENGTH: 6
<212> TYPE: PRT
<213> ORGANISM: Artificial Sequence
<220> FEATURE:
```

```
<223> OTHER INFORMATION: IMMUNE-ENHANCING PEPTIDE
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 9

Met Phe Tyr Leu Val Asp
1               5

<210> SEQ ID NO 10
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 10

Met Phe Tyr Leu Val Met
1               5

<210> SEQ ID NO 11
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 11

His Phe Tyr Leu Val Gly
1               5

<210> SEQ ID NO 12
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 12

His Phe Tyr Leu Val Asp
1               5

<210> SEQ ID NO 13
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: SITE
<222> LOCATION: (6)
<223> OTHER INFORMATION: Methionine residue optionally substituted
      with -NH2 group on carboxyl group
```

```
<400> SEQUENCE: 13

His Phe Tyr Leu Val Met
1               5

<210> SEQ ID NO 14
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Met
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 14

Met Phe Tyr Leu Pro Met
1               5

<210> SEQ ID NO 15
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Met
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 15

His Phe Tyr Leu Val Met
1               5

<210> SEQ ID NO 16
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Met
<220> FEATURE:
<221> NAME/KEY: SITE
<222> LOCATION: (6)
<223> OTHER INFORMATION: Methionine residue optionally substituted
      with -NH2 group on carboxyl group

<400> SEQUENCE: 16

Met Phe Tyr Leu Val Met
1               5

<210> SEQ ID NO 17
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
```

```
<221> NAME/KEY: MOD_RES
<222> LOCATION: (6)
<223> OTHER INFORMATION: D-Gly
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 17

His Phe Tyr Leu Pro Gly
1               5

<210> SEQ ID NO 18
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Asp
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 18

His Phe Tyr Leu Pro Asp
1               5

<210> SEQ ID NO 19
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Gly
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 19

Met Phe Tyr Leu Pro Gly
1               5

<210> SEQ ID NO 20
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Asp
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 20

Met Phe Tyr Leu Pro Asp
1               5
```

```
<210> SEQ ID NO 21
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Gly
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 21

His Phe Tyr Leu Pro Gly
1               5

<210> SEQ ID NO 22
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Asp
<220> FEATURE:
<221> NAME/KEY: SITE
<222> LOCATION: (6)
<223> OTHER INFORMATION: Aspartic acid residue optionally substituted
      with -NH2 group on carboxyl group

<400> SEQUENCE: 22

His Phe Tyr Leu Pro Asp
1               5

<210> SEQ ID NO 23
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Gly
<220> FEATURE:
<221> NAME/KEY: SITE
<222> LOCATION: (6)
<223> OTHER INFORMATION: Glycine residue optionally substituted with -NH2
      group on carboxyl group

<400> SEQUENCE: 23

Met Phe Tyr Leu Pro Gly
1               5

<210> SEQ ID NO 24
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MOD_RES
<222> LOCATION: (6)
<223> OTHER INFORMATION: D-Asp
<220> FEATURE:
```

```
<221> NAME/KEY: SITE
<222> LOCATION: (6)
<223> OTHER INFORMATION: Aspartic acid residue optionally substituted
      with -NH2 group on carboxyl group

<400> SEQUENCE: 24

Met Phe Tyr Leu Pro Asp
1               5

<210> SEQ ID NO 25
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: misc_feature
<222> LOCATION: (6)
<223> OTHER INFORMATION: Methionine residue optionally substituted
      with -NH2 group on carboxyl  group

<400> SEQUENCE: 25

Met Phe Tyr Leu Pro Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Methionine residue optionally substituted
      with -NH2 group on carboxyl group

<400> SEQUENCE: 26

His Phe Tyr Leu Pro Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Methionine residue optionally substituted
      with -NH2 group on carboxyl group

<400> SEQUENCE: 27

Met Phe Tyr Leu Val Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Methionine residue optionally substituted
      with -NH2 group on carboxyl group

<400> SEQUENCE: 28
```

```
His Phe Tyr Leu Val Xaa
1               5
```

<210> SEQ ID NO 29
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Aspartic acid or glycine residue optionally
      substituted with -NH2 group on carboxyl group

<400> SEQUENCE: 29

```
Met Phe Tyr Leu Pro Xaa
1               5
```

<210> SEQ ID NO 30
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Aspartic acid or glycine residue optionally
      substituted with -NH2 group on carboxyl group

<400> SEQUENCE: 30

```
His Phe Tyr Leu Pro Xaa
1               5
```

<210> SEQ ID NO 31
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Aspartic acid or glycine residue optionally
      substituted with -NH2 group on carboxyl group

<400> SEQUENCE: 31

```
Met Phe Tyr Leu Val Xaa
1               5
```

<210> SEQ ID NO 32
<211> LENGTH: 6
<212> TYPE: PRT
<213> ORGANISM: Artificial Sequence
<220> FEATURE:
<223> OTHER INFORMATION: IMMUNE-ENHANCING PEPTIDE
<220> FEATURE:
<221> NAME/KEY: MISC_FEATURE
<222> LOCATION: (6)
<223> OTHER INFORMATION: Aspartic acid or glycine residue optionally
      substituted with -NH2 group on
      carboxyl group

<400> SEQUENCE: 32

```
His Phe Tyr Leu Val Xaa
1               5
```